(12) United States Patent
Popovic et al.

(10) Patent No.: US 10,453,174 B2
(45) Date of Patent: *Oct. 22, 2019

(54) ENDOSCOPIC REGISTRATION OF VESSEL TREE IMAGES (71) Applicant: KONINKLIJKE PHILIPS N.V., Eindhoven (NL)

(72) Inventors: Aleksandra Popovic, New York, NY (US); Haytham Elhawary, New York, NY (US); Christopher Stephen Hall, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1060 days.

This patent is subject to a terminal disclaimer.

(21) Appl. No.: 14/353,776

(22) PCT Filed: Oct. 19, 2012

(86) PCT No.: PCT/IB2012/055739
§ 371 (c)(1),
(2) Date: Apr. 24, 2014

(87) PCT Pub. No.: WO2013/061225
PCT Pub. Date: May 2, 2013

(65) Prior Publication Data
US 2014/0301618 A1    Oct. 9, 2014

Related U.S. Application Data

(60) Provisional application No. 61/551,513, filed on Oct. 26, 2011.

(51) Int. Cl.
*A61B 90/00* (2016.01)
*G06T 7/00* (2017.01)
(Continued)

(52) U.S. Cl.
CPC ........ *G06T 3/0068* (2013.01); *A61B 1/00009* (2013.01); *A61B 90/37* (2016.02);
(Continued)

(58) Field of Classification Search
None
See application file for complete search history.

(56) References Cited

U.S. PATENT DOCUMENTS 6,711,433 B1 * 3/2004 Geiger ................... A61B 6/463
378/42
8,821,376 B2    9/2014 Tolkowsky
(Continued)

FOREIGN PATENT DOCUMENTS

JP    2006198032 A    8/2006
WO    WO199900052    1/1999
(Continued)

*Primary Examiner* — Jiangeng Sun (57) ABSTRACT

An image registration system employs an endoscope and an endoscope controller. In operation, the endoscope generates an intra-operative endoscopic image of a vessel tree (e.g., an arterial tree or a venous tree) within an anatomical region, and the endoscope controller image registers the intra-operative endoscopic image of the vessel tree to a pre-operative three-dimensional image of the vessel tree within the anatomical region. The image registration includes an image matching of a graphical representation of each furcation of the vessel tree within the intra-operative endoscopic image of the vessel tree to a graphical representation of each furcation of the vessel tree within the pre-operative three-dimensional image of the vessel tree.

13 Claims, 10 Drawing Sheets

(51) Int. Cl.
*G06T 3/00* (2006.01)
*A61B 1/00* (2006.01)
*G06T 19/00* (2011.01)
*A61B 34/30* (2016.01)

(52) U.S. Cl.
CPC ............ *G06T 7/0012* (2013.01); *G06T 19/00* (2013.01); *A61B 34/30* (2016.02); *A61B 2090/365* (2016.02); *A61B 2090/367* (2016.02); *G06T 2207/10068* (2013.01); *G06T 2207/30101* (2013.01)

(56) References Cited

U.S. PATENT DOCUMENTS

| | | | |
|---|---|---|---|
| 2007/0001879 A1* | 1/2007 | Kaftan et al. | 341/79 |
| 2011/0201915 A1* | 8/2011 | Gogin et al. | 600/407 |
| 2013/0158970 A1* | 6/2013 | Hof et al. | 703/11 |

FOREIGN PATENT DOCUMENTS

| | | |
|---|---|---|
| WO | WO2005025404 | 3/2005 |
| WO | WO 2005025404 A2 * | 3/2005 |
| WO | WO2010046838 | 4/2010 |

\* cited by examiner

ENDOSCOPIC REGISTRATION OF VESSEL TREE IMAGES

CROSS-REFERENCE TO PRIOR APPLICATIONS

This application is the U.S. National Phase application under 35 U.S.C. § 371 of International Application Serial No. PCT/IB2012/055739, filed on Oct. 19, 2012, which claims the benefit of U.S. Application Ser. No. 61/551,513, filed on Oct. 26, 2011. These applications are hereby incorporated by reference herein.

This application claims benefit to of the commonly-owned Patent Application entitled "Robotic Control of an Endoscope from Blood Vessel Tree Images," PCT/IB2011/053998, filed Sep. 13, 2011.

The present invention generally relates to an intra-operative registration between a pre-operative three-dimensional ("3D") vessel tree image to an intra-operative endoscopic vessel tree image. The present invention specifically relates to the intra-operative registration incorporating methods for addressing any change in topology of the vessel tree during a coronary surgical procedure.

Coronary artery bypass grafting ("CABG") is a surgical procedure for revascularization of obstructed coronary arteries. Approximately 500,000 operations are performed annually in the United States. In conventional CABG, the patient's sternum is opened and the patient's heart is fully exposed to a surgeon. Despite the exposure of the heart, some arteries may be partially invisible due to fatty tissue layer above them. For such arteries, the surgeon may palpate the heart surface and feel both blood pulsating from the arteries and a stenosis of the arteries. However, this data is sparse and might not be sufficient to transfer a surgical plan to the surgical site.

In minimally invasive CABG, the aforementioned problem of conventional CABG is amplified because a surgeon cannot palpate the heart surface. Additionally, the length of surgical instruments used in minimally invasive CABG prevents any tactile feedback from the proximal end of the tool.

One known technique for addressing the problems with conventional CABG is to register an intra-operative site with a pre-operative 3D coronary artery tree. Specifically, an optically tracked pointer is used to digitalize position of the arteries in an open heart setting and the position data is registered to pre-operative tree using an Iterative Closest Point ("ICP") algorithm known in art. However, this technique, as with any related approach matching digitized arteries and pre-operative data, is impractical for minimally invasive CABG because of spatial constraints imposed by a small port access. Also, this technique requires most of the arteries to be either visible or palpated by the surgeon, which is impossible in minimally invasive CABG.

One known technique for addressing the problems with minimally invasive CABG is to implement a registration method in which the heart surface is reconstructed using an optically tracked endoscope and matched to pre-operative computer tomography ("CT") data of the same surface. However, this technique, as with any related approach proposing surface based matching, may fail if the endoscope view used to derive the surface is too small. Furthermore, as the heart surface is relatively smooth without specific surface features, the algorithm of this technique more often than not operates in a suboptimal local maximum of the algorithm.

Another known technique for addressing the problems with minimally invasive CABG is to label a coronary tree extracted from a new patient using a database of previously labeled cases and graph based matching. However, this technique works only if a complete tree is available and it's goal is to label the tree rather to match the geometry.

A further problem of minimally invasive CABG is an orientation and a guidance of the endoscope once the global positioning with respect to pre-operative 3D images is reached. The goal of registration is to facilitate localization of the anastomosis site and the stenosis. In a standard setup, the endoscope is being held by an assistant, while the surgeon holds two instruments. The surgeon issues commands to the assistant and the assistant moves the endoscope accordingly. This kind of setup hinders hand-eye coordination of the surgeon, because the assistant needs to intuitively translate surgeon's commands, typically issued in the surgeon's frame of reference, to the assistant's frame of reference and the endoscope's frame of reference. Plurality of coordinate systems may cause various handling errors, prolong the surgery or cause misidentification of the coronary arteries.

A surgical endoscope assistant designed to allow a surgeon to directly control an endoscope via a sensed movement of the surgeon head may solve some of those problems by removing the assistant from the control loop, but the problem of transformation between the surgeon's frame of reference and the endoscope's frame of reference remains.

The present invention provides image registration methods for matching graphical representations at each furcation of a vessel tree (e.g., each point of arteries, capillaries, veins and other multi-branched anatomical structures) as shown in a pre-operative three-dimensional ("3D") image (e.g., a CT image, a cone beam CT image, a 3D X-Ray images or a MRI image) and in an intra-operative endoscopic image. The image registration methods may further address any change in topology of the vessel tree during a surgical procedure, particularly a CABG.

For purposes of the present invention, the term "furcation" is broadly defined herein as any point along a vessel tree that divides into two or more branches.

One form of the present invention is a registration system employing an endoscope and an endoscope controller. In operation, the endoscope generates an intra-operative endoscopic image of a vessel tree (e.g., an arterial tree, a venous tree or any other tubular structure of the human body) within an anatomical region, and the endoscope controller image registers the intra-operative endoscopic image of the vessel tree to a pre-operative three-dimensional image of the vessel tree. The image registration includes an image matching of a graphical representation of each furcation of the vessel tree within the intra-operative endoscopic image of the vessel tree to a graphical representation of each furcation of the vessel tree within the pre-operative three-dimensional image of the vessel tree.

A second form of the present invention is an image registration method involving a generation of a pre-operative three-dimensional image of a vessel tree within an anatomical region, a generation of an intra-operative endoscopic image of the vessel tree within the anatomical region, and image registration of the intra-operative endoscopic image of the vessel tree to the pre-operative three-dimensional image of the vessel tree. The image registration includes an image matching of a graphical representation of each furcation of the vessel tree within the intra-operative endoscopic image of the vessel tree to a graphical representation of each furcation of the vessel tree within the pre-operative three-dimensional image of the vessel tree.

The term "pre-operative" as used herein is broadly defined to describe any activity executed before, during or after an endoscopic imaging of an anatomical region for purposes of acquiring a three-dimensional image of the anatomical region, and the term "intra-operative" as used herein is broadly defined to describe any activity during or related to an endoscopic imaging of the anatomical region. Examples of an endoscopic imaging of an anatomical region include, but are not limited to, a CABG, a bronchoscopy, a colonscopy, a laparascopy, and a brain endoscopy.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
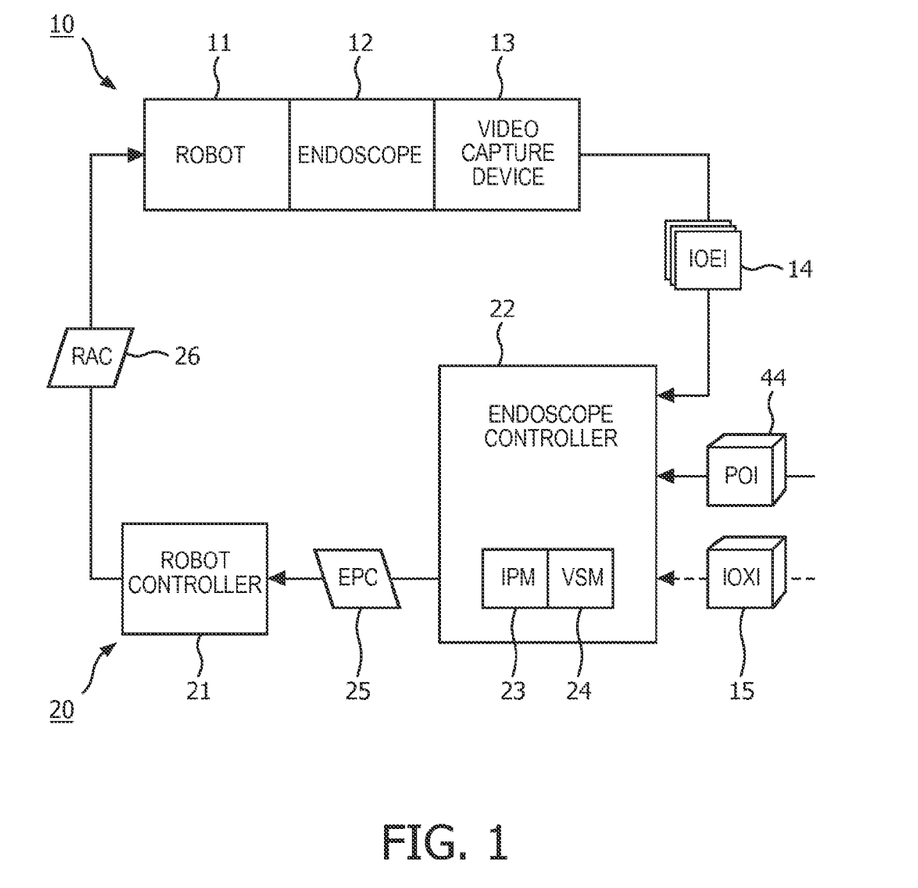
FIG. 1 illustrates an exemplary embodiment of a robotic guiding system in accordance with the present invention.

As shown in FIG. 1, a robotic guiding system employs a robot unit 10 and a control unit 20 for any endoscopic procedure involving an endoscopic imaging of a vessel tree having one or more furcations (i.e., branches). Examples of such endoscopic procedures include, but are not limited to, minimally invasive cardiac surgery (e.g., coronary artery bypass grafting or mitral valve replacement).

Robot unit 10 includes a robot 11, an endoscope 12 rigidly attached to robot 11 and a video capture device 13 attached to the endoscope 12.

Robot 11 is broadly defined herein as any robotic device structurally configured with motorized control of one or more joints for maneuvering an end-effector as desired for the particular endoscopic procedure. In practice, robot 11 may have four (4) degrees-of-freedom, such as, for example, a serial robot having joints serially connected with rigid segments, a parallel robot having joints and rigid segments mounted in parallel order (e.g., a Stewart platform known in the art) or any hybrid combination of serial and parallel kinematics.

Endoscope 12 is broadly defined herein as any device structurally configured with ability to image from inside a body. Examples of endoscope 12 for purposes of the present invention include, but are not limited to, any type of scope, flexible or rigid (e.g., endoscope, arthroscope, broncho-scope, choledochoscope, colonoscope, cystoscope, duo-denoscope, gastroscope, hysteroscope, laparoscope, laryn-goscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, and miniaturized (e.g. CCD based) imaging systems.

In practice, endoscope 12 is mounted to the end-effector of robot 11. A pose of the end-effector of robot 11 is a position and an orientation of the end-effector within a coordinate system of robot 11 actuators. With endoscope 12 mounted to the end-effector of robot 11, any given pose of the field-of-view of endoscope 12 within an anatomical region corresponds to a distinct pose of the end-effector of robot 11 within the robotic coordinate system. Consequently, each individual endoscopic image of a vessel tree generated by endoscope 12 may be linked to a corresponding pose of endoscope 12 within the anatomical region.

Video capture device 13 is broadly defined herein as any device structurally configured with a capability to convert an intra-operative endoscopic video signal from endoscope 12 into a computer readable temporal sequence of intra-operative endoscopic images ("IOEI") 14. In practice, video capture device 13 may employ a frame grabber of any type for capturing individual digital still frames from the intra-operative endoscopic video signal.

Still referring to FIG. 1, control unit 20 includes a robot controller 21 and an endoscope controller 22.

Robot controller 21 is broadly defined herein as any controller structurally configured to provide one or more robot actuator commands ("RAC") 26 to robot 11 for controlling a pose of the end-effector of robot 11 as desired for the endoscopic procedure. More particularly, robot controller 21 converts endoscope position commands ("EPC") 25 from endoscope controller 22 into robot actuator commands 26. For example, endoscope position commands 25 may indicate an endoscopic path leading to desired 3D position of a field-of-view of endoscope 12 within an anatomical region whereby robot controller 21 converts command 25 into commands 26 including an actuation current for each motor of robot 11 as needed to move endoscope 12 to the desired 3D position.

Figure 2:
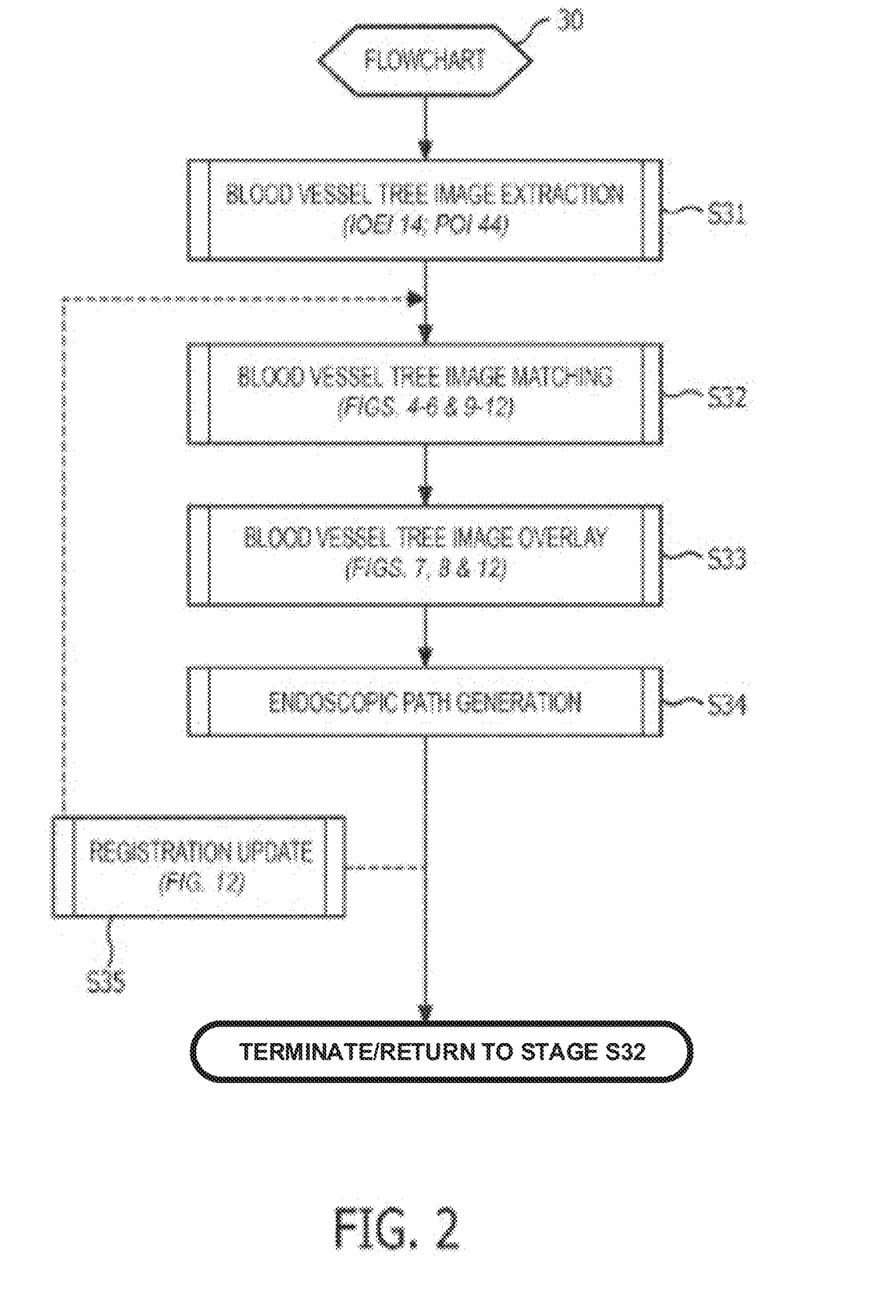
FIG. 2 illustrates a flowchart representative of an exemplary embodiment of a robotic guidance method in accordance with the present invention.

Endoscope controller 22 is broadly defined herein as any controller structurally configured for implementing a robotic guidance method in accordance with the present invention as exemplary shown in FIG. 2 (e.g., an application specific main board or an application specific integrated circuit structurally configured to implement the robotic guidance method in accordance with the present invention as exemplary shown in FIG. 2). To this end, endoscope controller 22 may incorporate an image processing module ("IPM") 23, which is broadly defined herein as any module structurally configured for executing an anatomical object image registration of the present invention (e.g., an electronic circuit and/or an executable program stored on a non-transitory computer readable medium and/or firmware for executing an anatomical object image registration of the present invention). In particular, a vessel tree image registration as exemplarily implemented by stages S32 and S33 of flowchart 30 shown in FIG. 2. Endoscope controller 22 may further incorporate a visual servo module ("VSM") 24, which is broadly defined herein as any module structurally configured for generating endoscope position commands 25 indicating an endoscopic path leading to desired 3D position of a field-of-view of endoscope 12 within an anatomical region (e.g., an electronic circuit and/or an executable program stored on a non-transitory computer readable medium and/or firmware for generating endoscope position commands 25). In particular, endoscope position commands 25 are derived from the vessel tree image registration as exemplarily implemented by a stage S34 of flowchart 30 shown in FIG. 2.

A description of flowchart 30 will now be provided herein to facilitate a further understanding of endoscope controller 22.

Figure 3:
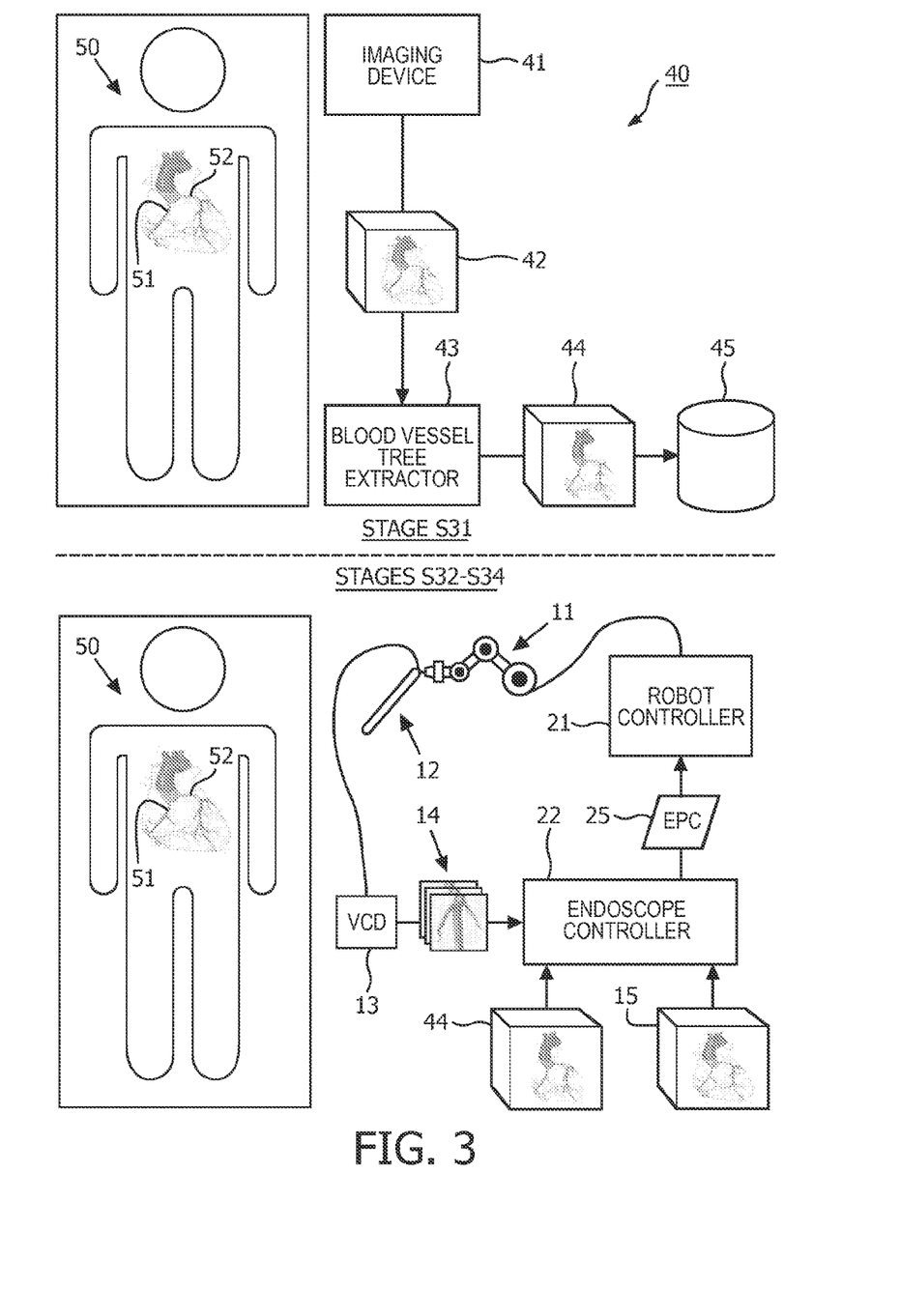
FIG. 3 illustrates an exemplary surgical implementation of the flowchart shown in FIG. 2

Referring to FIG. 2, a stage S31 of flowchart 30 encompasses an extraction of a geometrical representation of a vessel tree (e.g., furcation of arteries, capillaries or veins) from a pre-operative 3D image of any anatomical region of a body. For example, as shown in FIG. 3, a 3D imaging device 41 (e.g., a CT device, an X-ray device, or a MRI device) is operated to generate a pre-operative 3D image 42 of a chest region of a patient 50 illustrating left and right coronary arteries 51 and 52 of patient 50. Thereafter, a vessel tree extractor 43 is operated to extract a geometrical representation 44 of a coronary arterial tree from image 42, which may be stored in a database 45. In practice, a Brilliance iCT scanner sold by Philips may be used to generate image 42 and to extract a 3D dataset of the coronary arterial tree from image 42.

Referring back to FIG. 2, a stage S32 of flowchart 30 encompasses image processing module 23 matching the graphical representation of one or more intra-operative endoscopic images 14 (FIG. 1) of the vessel tree to a graphical representation of pre-operative 3D image 44 (FIG. 1) of the vessel tree. For example, as shown in FIG. 3, endoscope 12 generates an intra-operative endoscopy video of a chest region of patient 50 that is captured by video capture device 13 and converted into intra-operative endoscopic images 14 whereby image processing module 23 of endoscope controller 22 matches a graphical representation of the intra-operative endoscopic image(s) 14 of the coronary arterial tree to a graphical representation of pre-operative 3D image 44 of the coronary arterial tree. In one exemplary embodiment, image processing module 23 executes a vessel tree image matching method of the present invention as exemplarily represented by a flowchart 60 shown in FIG. 4, which will be described herein in the context of the vessel tree being a coronary arterial tree.

Figure 4:
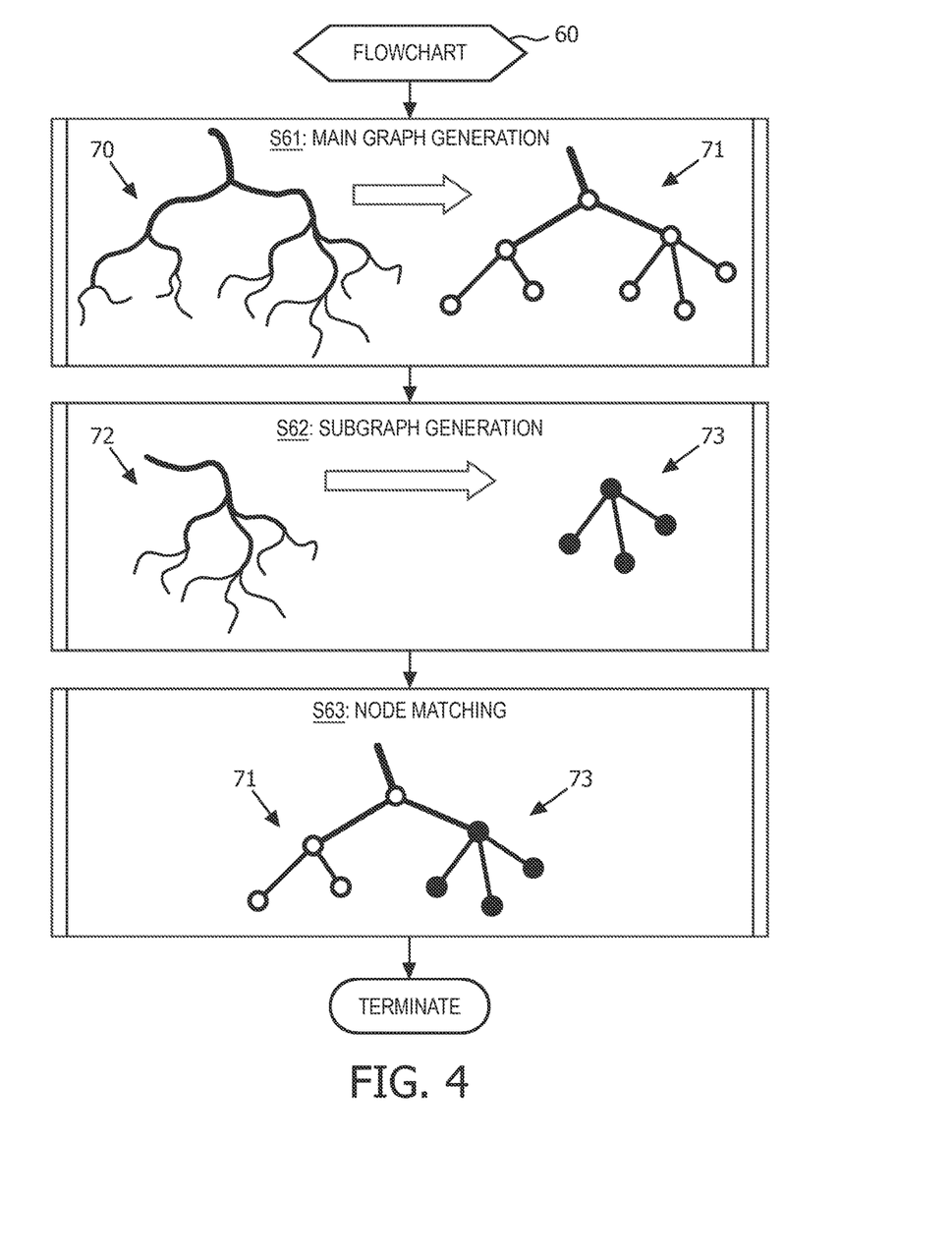
FIG. 4 illustrates a flowchart representative of an exemplary embodiment of a graph matching method in accordance with the present invention.

Referring to FIG. 4, (the blood vessel) a stage S61 of flowchart 60 encompasses image processing module 23 generating a coronary arterial tree main graph from a geometrical representation of the coronary arterial tree in accordance with any representation method known in the art. For example, as shown in stage S61, a geometrical representation 70 of a coronary arterial tree is converted into a main graph 71 having nodes represented of each furcation (e.g., a bifurcation or trifurcation) of coronary arterial tree geometrical representation 70 and further having branch connections between nodes. Stage S61 may be performed pre-operatively (e.g., days before the endoscopic surgery or any time prior to an introduction of endoscope 12 within patient 50), or intra-operatively by means of a C-arm angiography or other suitable system.

A stage S62 of flowchart 60 encompasses image processing module 23 generating a coronary arterial tree subgraph from a portion of a coronary arterial tree visible in an intra-operative endoscopic image 14 in accordance with any graphical representation method known in the art. Specifically, endoscope 12 is introduced into patient 50 whereby image processing module 23 performs a detection of a coronary arterial structure within the intra-operative endoscopic image 14. In practice, some arterial structures may be visible while other arterial structures may be hidden by a layer of fatty tissue. As such, image processing module 23 may implement an automatic detection of visible coronary arterial structure(s) by known image processing operations (e.g., threshold detection by the distinct red color of the visible coronary arterial structure(s)), or a surgeon may manually use an input device to outline the visible coronary arterial structure(s) on the computer display. Upon a detection of the arterial structure(s), image processing module 23 generates the coronary arterial tree graph in a similar manner to the generation of the coronary arterial tree main graph. For example, as shown in stage S62, a geometrical representation 72 of coronary arterial structure(s) is converted into a graph 73 having nodes represented of each furcation (e.g., a bifurcation or trifurcation) of coronary arterial tree geometrical representation 72 and further having branch connections between nodes. Since both trees are coming from the same person, it is understood that the graph derived from endoscopy images is a subgraph of the graph derived from 3D images.

A stage S63 of flowchart 60 encompasses image processing module 23 matching the subgraph to the maingraph in accordance with any known graph matching methods (e.g., a maximum common subgraph or a McGregor common subgraph). For example, as shown in stage S63, the nodes of subgraph 73 are matched to a subset of nodes of main graph 71.

In practice, subgraph 73 may only be partially detected within intra-operative endoscopic image 14 or some nodes/connections of subgraph 73 may be missing from intra-operative endoscopic image 14. To improve upon the matching accuracy of stage S62, an additional ordering of main graph 71 and subgraph 73 may be implemented.

Figure 5:
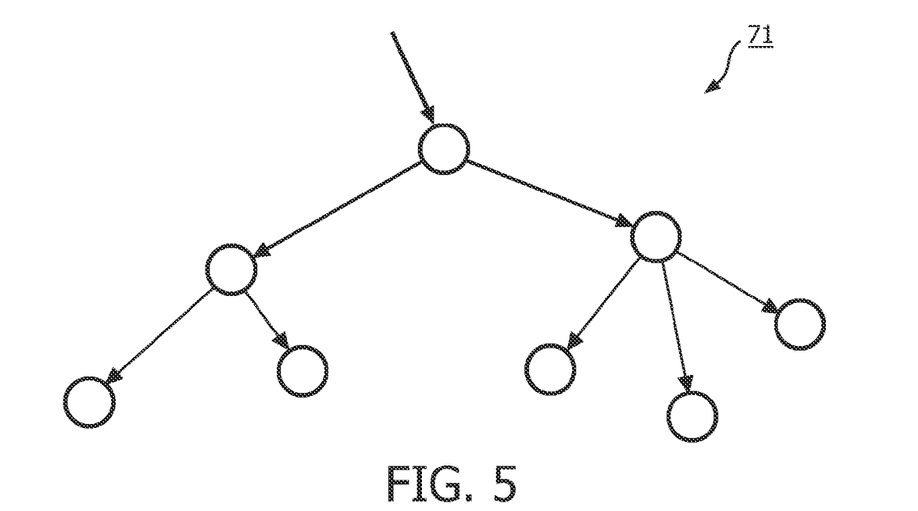
FIGS. 5 and 6 illustrate an exemplary ordering of main graphs of a vessel tree in accordance with the present invention.

In one embodiment, a vertical node ordering of main graph 71 is implemented based on a known orientation of patient 50 during the image scanning of stage S61. Specifically, the main graph nodes may be directionally linked to preserve a top-bottom order as exemplarily shown in FIG. 5 via the solid arrows. For subgraph 73, the orientation of patient 50 relative to endoscope 12 may not be known. However, knowing that branches of the coronary arterial tree reduce in diameter as they expand top-bottom, then varying arterial sizes of the arterial branches in intra-operative endoscopic image 14 may indicate orientation.

Figure 6:
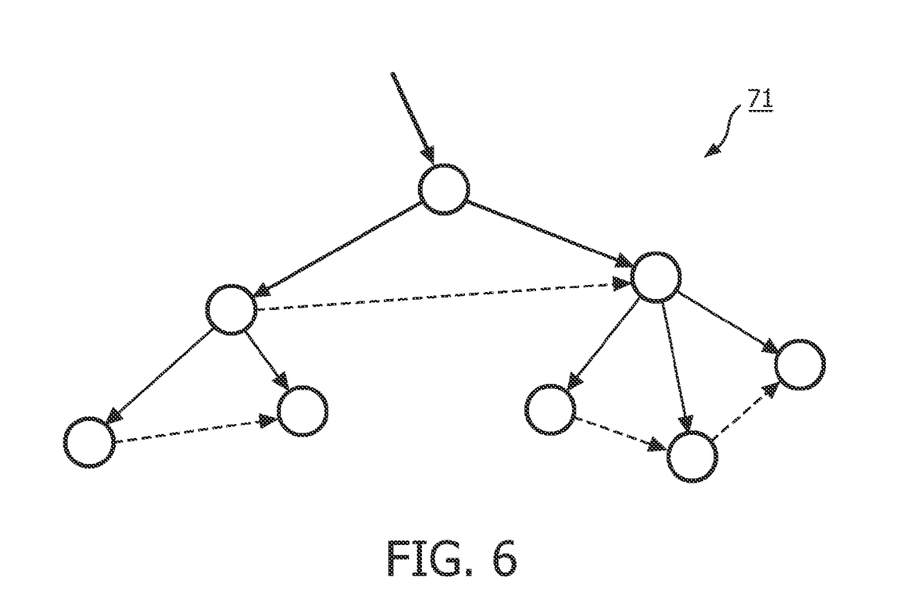

In another embodiment, a horizontal node ordering of main graph 70 may be implemented based on the known orientation of patient 50 during the image scanning of stage S61. Specifically, the main graph nodes may be directionally linked to preserve a left-right node order as exemplarily shown in FIG. 6 via the dashed arrows. For subgraph 73, with the orientation of patient 50 to endoscope 12 more than likely being unknown, the horizontal node order of subgraph 73 may be set by the operating surgeon or an assistant via a graphical user interface.

While the use of ordering may decrease the time for matching the graphs and reduce the number of possible matches, theoretically multiple matches between the graphs may still be obtained by the matching algorithm. Such a case of multiple matches is addressed during a stage S33 of flowchart 30.

Referring again to FIG. 2, based on the matching of the graphs, a stage S33 of flowchart encompasses an overlay of the geometrical representation of pre-operative 3D image 44 (FIG. 1) of the vessel tree on the intra-operative endoscopic image 14 of the vessel tree. This is done by using the geometrical representation uniquely associated to the main-graph. Thus, the entire geometry may be directly translated to intra-operative endoscopic image 14 using a perspective transformation. The perspective transformation may be detected from intra-operative endoscopic image 14 and nodes in pre-operative 3D image 44 using matching algorithms known in art (e.g., a homography matching).

Figure 7:
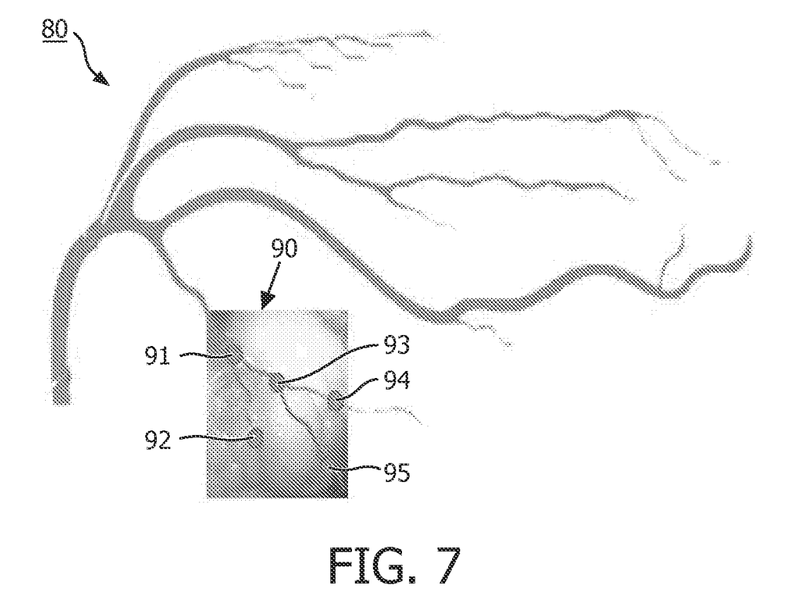
FIG. 7 illustrates an exemplary overlay of a geometrical representation on an endoscopic image accordance with the present invention.

For example, FIG. 7 illustrates a geometrical representation 80 of a coronary arterial tree having nodes matched to nodes 91-95 with an intra-operative endoscopic image 90. The distance between each node pair among nodes 91-95 may be used to determine a scaling factor for geometrical representation 80 to thereby enable geometrical representation 80 to overlay intra-operative endoscopic image 90 as shown.

In practice, if the graph matching of stage S32 (FIG. 2) yields multiple results, then all possible overlays may be displayed to the surgeon whereby the surgeon may select the matching result the surgeon believes is the most likely match via a graphical user interface. Given that the surgeon knows the position of endoscope 12 relative to at least some structures in intra-operative endoscopic image 14, the selection may be relatively straightforward.

Figure 8:
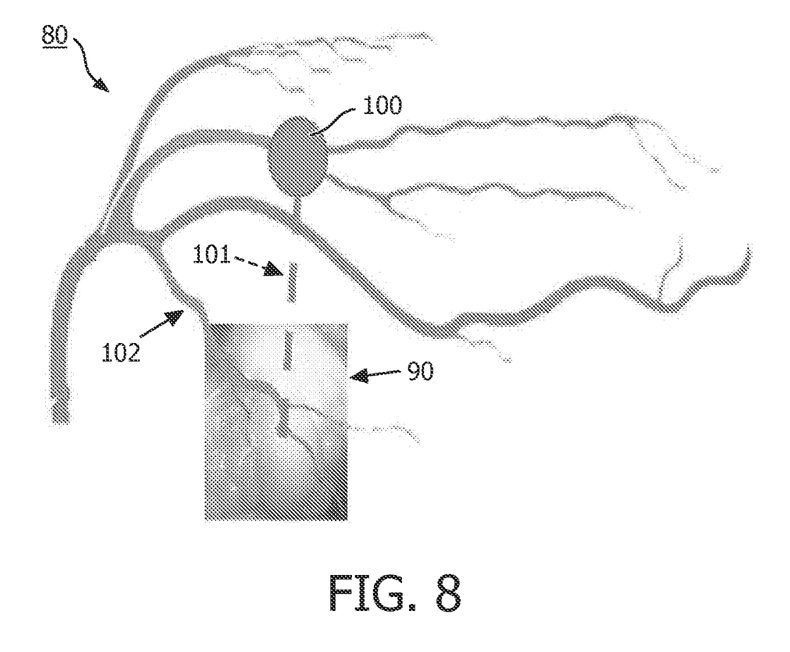
FIG. 8 illustrates an exemplary robot paths within the overlay shown in FIG. 7 in accordance with the present invention.

Referring back to FIG. 2, a stage S34 of flowchart 30 encompasses visual servo module 24 generating an endoscopic path within the overlay of the geometrical representation of pre-operative 3D image 44 (FIG. 1) of the vessel tree on intra-operative endoscopic image 14 (FIG. 1) of the vessel tree. Based on the endoscopic path, visual servo module 24 generates endoscope position commands 25 to robot controller 21 to thereby guide endoscope 12 (FIG. 1) along the endoscopic path to a desired position within the anatomical region. Specifically, once the exact overlay is found, robot 11 may be commanded to guide endoscope 12 to positions the surgeon selects on pre-operative 3D image 44. The surgeon or the assistant may select a point of vessel tree, and robot 11 may guide endoscope 12 towards that desired position along any suitable path. For example, as shown in FIG. 8, robot 11 may move endoscope 12 along a shortest path 101 to a desired position 100 or along an coronary arterial path 102 to desired position 100. Coronary arterial path 102 is the preferred embodiment, because coronary arterial path 102 allows the surgeon to observe visible arteries as robot 11 moves endoscope 12. In addition, it might help the surgeon to decide if the matching was successful. Coronary arterial path 102 may be defined using methods known in art (e.g., Dijkstra shortest path algorithm).

In practice, the movement of robot 11 may be commanded using uncalibrated visual servoing with remote center of motion, and the field of view of endoscope 12 may be extended to enable a larger subgraph during matching stage S32 (e.g., a stitching of intra-operative endoscopic images 14 as known in the art).

As previously described herein, stages 32 and 33 of flowchart 30 as shown in FIG. 2 represents a vessel tree image registration of the present invention involving a single vessel tree. Additionally, the previous description of stages S32 and S33 was provided in the context of a coronal arterial tree to facilitate an understanding of stages S32 and S33. In practice, vessel tree image registration of the present invention may involve two (2) or more blood vessels trees of any type within any anatomical region of the body.

Figure 9:
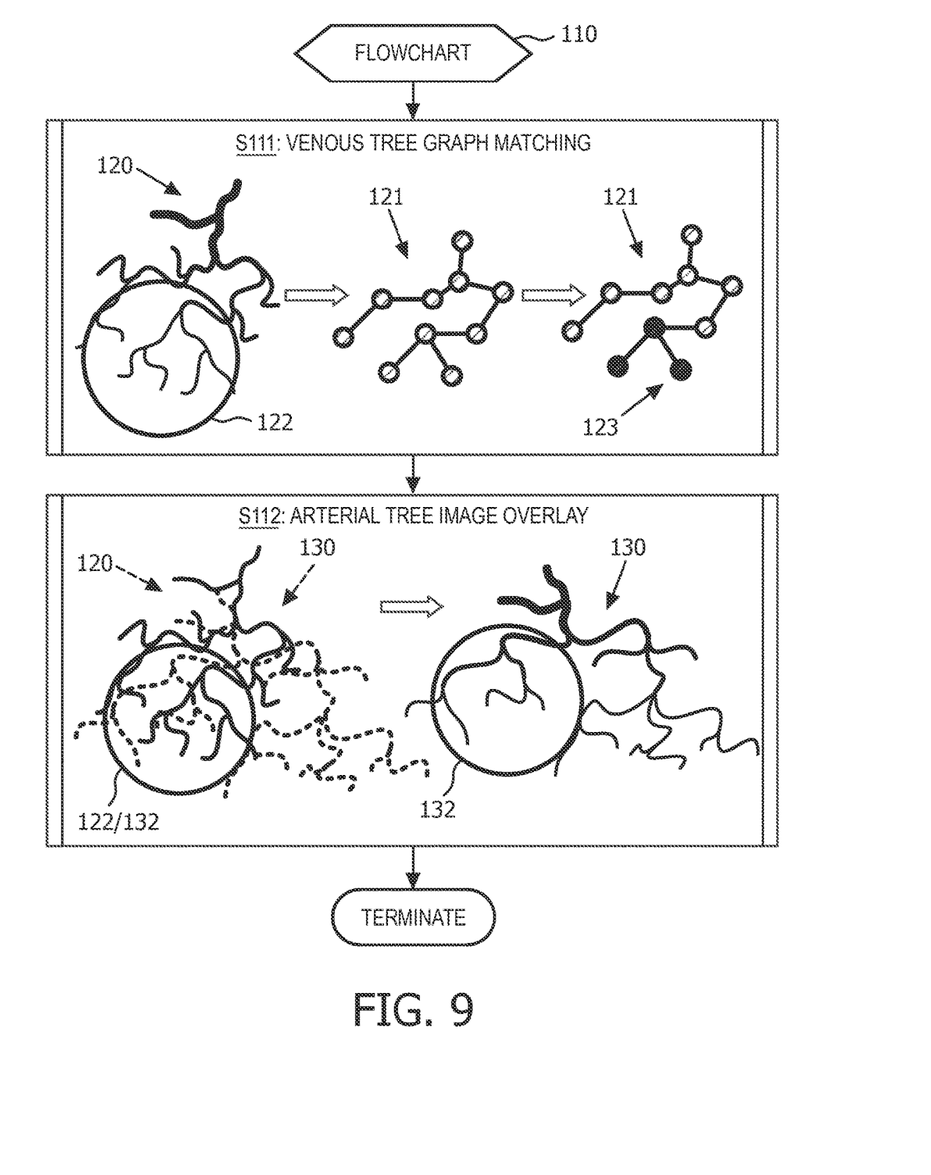
FIG. 9 illustrates a flowchart representative of a venous registration method in accordance with the present invention.
Figure 10:
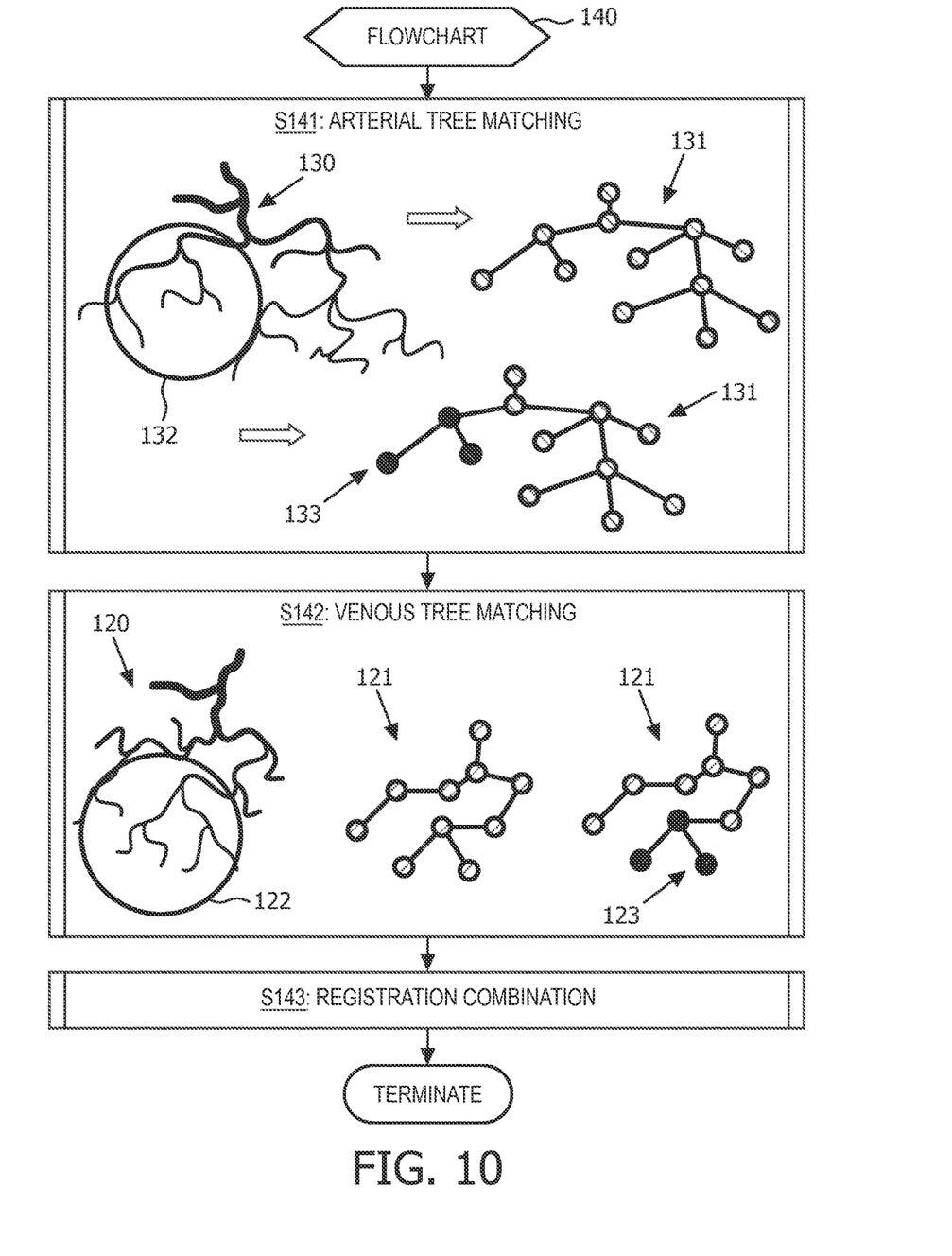
FIG. 10 illustrates a flowchart representative of a first embodiment of a venous/arterial integrated registration method in accordance with the present invention.
Figure 11:
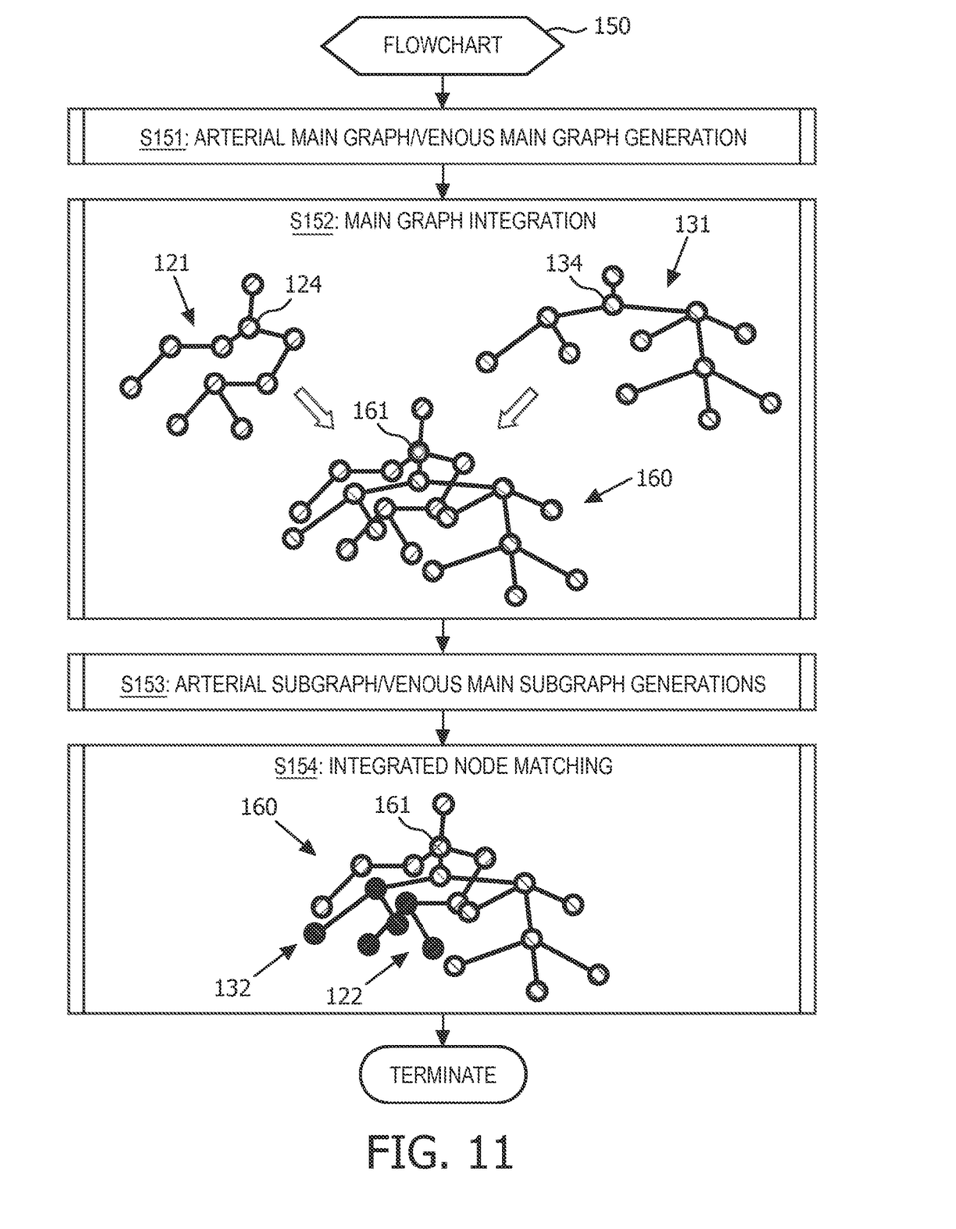
FIG. 11 illustrates a flowchart representative of a second embodiment of a venous/arterial integrated registration method in accordance with the present invention.

FIGS. 9-11 illustrate additional embodiments of stage 32 and/or stage S33 (FIG. 2) in the context of an arterial tree and a venous tree within any anatomical region of the body, particularly the coronary region. These embodiments perform graph generation and node matching in accordance with the principles of flowchart 60 (FIG. 4) as previously taught herein.

Referring to FIG. 9, a flowchart 111 represents a venous tree image registration method involving a matching of a main graph of an intra-operative endoscopic image of venous tree to a pre-operative image of the venous tree that serves as a basis for registering intra-operative endoscopic images of the anatomical region to a pre-operative 3D image of the anatomical region.

Specifically, a stage S111 of flowchart 110 encompasses image processing module 23 executing a venous tree graph matching between an intra-operative endoscopic image of venous tree to a pre-operative 3D image of the venous tree. For example as shown in stage S111 of FIG. 9, a main graph 121 of a pre-operative 3D image 120 of a venous tree and a subgraph 123 of an intra-operative endoscopic image 122 of the venous tree are generated, and the nodes of subgraph 123 of matched to a particular subset of the nodes of main graph 121. The result is a registration of intra-operative endoscopic images of the anatomical region to the pre-operative 3D image of the anatomical region.

A stage S112 of flowchart 110 encompasses image processing module 23 executing a generation as known in the art of an overlay of a pre-operative image of the arterial tree that is derived from a relative positioning of the arterial tree to the venous tree within the pre-operative image of the anatomical region. For example as shown in stage S112 of FIG. 9, an overlay of pre-operative image 130 of the arterial tree onto an intra-operative endoscopic image 132 of the arterial tree is derived from a relative positioning of a pre-operative image 130 of the arterial tree (shown in dashed lines) to pre-operative image 120 of the venous tree.

Referring to FIG. 10, a flowchart 140 represents a blood tree image registration method involving a combination of (1) an arterial tree matching of a subgraph of an intra-operative endoscopic image of the arterial tree to a main graph of a pre-operative image of the arterial and of (2) a venous tree matching of a subgraph of an intra-operative endoscopic image of the venous tree to a main graph of the pre-operative image of the venous tree.

Specifically, a stage S141 of flowchart 140 encompasses image processing module 23 executing an arterial tree graph matching between an intra-operative endoscopic image of the arterial tree to a pre-operative 3D image of the arterial tree. For example, as shown in stage S141 of FIG. 10, a main graph 131 of pre-operative 3D image 130 of the arterial tree and a subgraph 133 of an intra-operative endoscopic image 132 of the arterial tree are generated, and the nodes of subgraph 133 of matched to a particular subset of the nodes of main graph 131.

A stage S142 of flowchart 140 encompasses image processing module 23 executing a venous tree graph matching between an intra-operative endoscopic image of venous tree to a pre-operative 3D image of the venous tree. For example as shown in stage S142 of FIG. 10, main graph 121 of pre-operative 3D image 120 of a venous tree and a subgraph 123 of an intra-operative endoscopic image 122 of the venous tree are generated, and the nodes of subgraph 123 of matched to a particular subset of the nodes of main graph 121.

A stage S143 of flowchart 140 encompasses image processing module geometrically combining the arterial tree matching of stage S141 and the venous tree matching of stage S142 as known in the art.

In practice, stages S141 and S142 may be serially executed in any order, or executed in parallel.

Referring to FIG. 11, a flowchart 150 represents a blood tree image registration method involving an integration of (1) an arterial tree matching of a subgraph of an intra-operative endoscopic image of the arterial tree to a main graph of a pre-operative image of the arterial and of (2) a venous tree matching of a subgraph of an intra-operative endoscopic image of the venous tree to a main graph of the pre-operative image of the venous tree.

Specifically, a stage S151 of flowchart 150 encompasses image processing module 23 generating main graphs of the arterial tree and the venous tree from respective pre-operative images of the arterial tree and the venous tree, and a stage S152 of flowchart 150 encompasses an integration of the main graphs of the arterial tree and the venous tree. In practice as related to the cardiac region, there is no single vessel point in which the arterial tree and the venous tree are actually connected. As such, the main graphs of the arterial tree and the venous tree are essentially disconnected. Nonetheless, there may be multiple points within the cardiac region anatomy where both an arterial node and a venous node are at an inconsequential distance apart. Theses nodes may be considered coincidental for purposes of stage S152, and thus a single tree joined at these nodes may be constructed.

For example, as shown in stage S152 of FIG. 11, a node 124 of a main graph 121 of the venous tree and a node 134 of a main graph 131 of the arterial tree at an inconsequential distance apart within the pre-operative volumetric image of the cardiac region, and therefore are joined at point 161 within the pre-operative volumetric image of the cardiac region to form an integrated vessel tree graph 160.

A stage S153 of flowchart 150 encompasses image processing module 23 generating subgraphs of the arterial tree and the venous tree from respective intra-operative endoscopic images of the arterial tree and the venous trees, and a stage S154 of flowchart 150 encompasses a node matching of the subgraphs of the arterial tree and the venous tree to the integrated blood vessel graph. For example as show in stage S154 of FIG. 11, a generated subgraph 132 of the arterial tree and a generated subgraph 122 of the venous tree are matched to the integrated vessel tree graph 160.

In practice, alternatively the integration of the main graphs of the vessel trees may occur at the individual matching of the subgraphs of the vessel trees to the respective main graphs.

Referring back to FIG. 2, stages S32-S34 may either be executed one time, or on a periodical basis until such time robot 11 has moved endoscope 12 to the desired position within the anatomical region, or multiple times as dictated by the surgeon.

In an alternative embodiment of flowchart 130, a stage S35 may be executed for purposes of updating the image registration as surgery is performed on the one or more of the blood trees within the anatomical region, particularly a cardiac region. For example, after a bypass is completed, the newly introduced topology of an arterial tree will be visible in an intra-operative surgical image (e.g., an endoscopic image or an X-ray angiographic image) of the bypass in the cardiac region and will not be visible on the pre-operative volumetric image of the cardiac region. The arterial tree from the intra-operative surgical image is matched with the arterial tree from the preoperative volumetric image using graph matching algorithm of the present invention as previously described herein. Upon the registration, the main graph of the pre-operative volumetric image may be updated by adding one new node (distal anastomosis site) and one connection (bypass) to the main graph.

Figure 12:
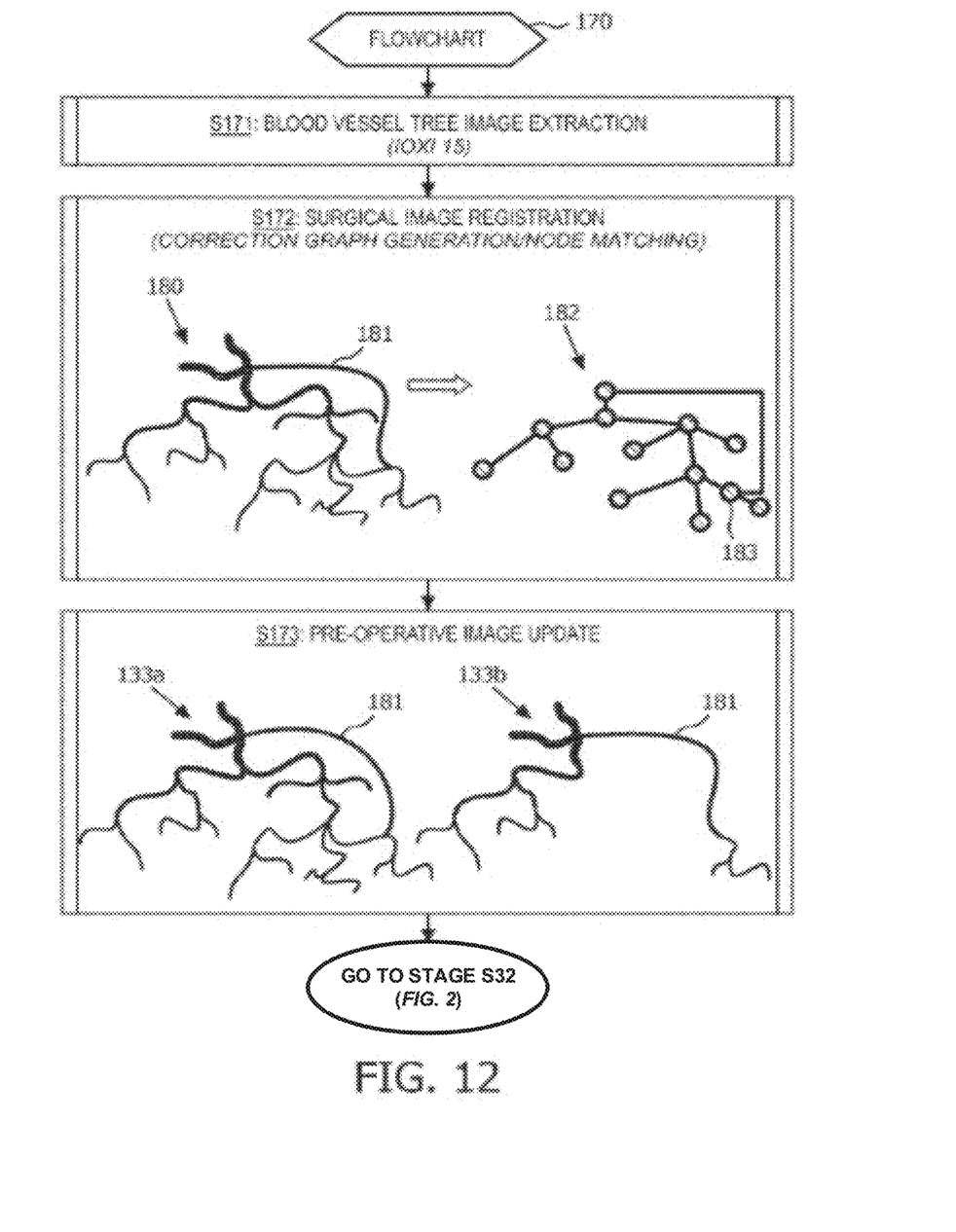
FIG. 12 illustrates a flowchart representative of a second embodiment of a registration correction method in accordance with the present invention.

A flowchart 170 shown in FIG. 12 represents one embodiment of stage S35 and stage S31 (FIG. 2). A stage S171 of flowchart 170 encompasses an extraction of a vessel tree from the intra-operative surgical image of the anatomical region and a stage S172 encompasses a registration of the intra-operative surgical image to the pre-operative volumetric image. For example as shown in stage S172 of FIG. 12, a surgical image 180 of arterial tree 133 is extracted from an intra-operative endoscopic image 14 or an intra-operative X-ray angiographic image 15 of the cardiac region with image 180 illustrating a bypass 181. A main graph 182 of image 180 is generated with a new connected node 183 representative of the bypass. Main graph 182 is node matched with a main graph of the pre-operative volumetric image (e.g., arterial tree image 130 and main graph 131 as shown in FIG. 10).

A stage S173 of flowchart 170 encompasses an update of the pre-operative volumetric image. In practice, the updated image 133 may full illustrate the complete arterial tree or may eliminate the bypassed portion of the complete arterial tree. For example, as shown in stage S173 of FIG. 12, an updated image 133*a* of the pre-operative volumetric image 133 illustrates the complete arterial tree including the bypass 181 or an updated image 134*b* of the pre-operative volumetric image 133 illustrates the arterial tree exclusive of the bypassed portion of the arterial tree.

Flowchart 170 returns to stage S32 (FIG. 2) where the updated image 133 may be used to re-register the intra-operative endoscopic image 14 to the pre-operative volumetric image 44 and guide robot 11 during stages S32-S34.

Referring back to FIG. 1, in practice, modules 23 and 24 may be implemented by hardware, software and/or firmware integrated within endoscope controller 22 as shown.

From the description of FIGS. 1-12 herein, those having ordinary skill in the art will appreciate the numerous benefits of the present invention including, but not limited to, an application of the present invention to any type of endoscopy surgery performed on any type of blood vessels.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. An image registration system, comprising:
    an endoscope operable for generating an intra-operative endoscopic image of a vessel tree within an anatomical region; and
    an endoscope controller structurally configured to image register the intra-operative endoscopic image of the vessel tree to a pre-operative three-dimensional image of the vessel tree responsive to a generation of the intra-operative endoscopic image of the vessel tree,
wherein an image registration by the endoscope controller includes an image matching by the endoscope controller of a graphical representation of each furcation of the vessel tree within the intra-operative endoscopic image of the vessel tree to a graphical representation of each furcation of the vessel tree within the pre-operative three-dimensional image of the vessel tree;
wherein the image matching by the endoscope controller includes:
a generation by the endoscope controller of a main graph derived from a geometrical representation of the pre-operative three-dimensional image of the vessel tree, the main graph including a main set of connected nodes representative of each furcation of the vessel tree within the pre-operative three-dimensional image of the vessel tree;
a generation by the endoscope controller of a subgraph derived from a geometrical representation of the intra-operative endoscopic image of the vessel tree, the subgraph including a subset of the main set of connected nodes and being representative of each furcation of the vessel tree within the intra-operative endoscopic image of the vessel tree; and
a node matching by the endoscope controller of the subgraph to the main graph, wherein the endoscope controller is further structurally configured to update the image registration of the intra-operative endoscopic image of the vessel tree to the pre-operative three-dimensional image of the vessel tree responsive to any surgical alteration in a topology of the vessel tree;
wherein the main graph by the endoscope controller is modified to reflect a surgical alteration in the topology of the vessel tree; and
wherein the modifying of the arterial main graph by the endoscope controller includes at least one of (1) a connecting by the endoscope controller of an additional node to the main graph, the new node being representative of a surgical creation of an additional furcation of the vessel tree, and (2) a disconnecting by the endoscope controller of one of the nodes of the main graph, the disconnected node being representative of a surgical removal of one of the furcations of the vessel tree.

2. The image registration system of claim 1, wherein the endoscope controller is further structurally configured to update the image registration of the intra-operative endoscopic image of the vessel tree to the pre-operative three-dimensional image of the vessel tree responsive to any surgical alteration in a topology of the vessel tree.

3. An image registration system, comprising:
an endoscope operable for generating an intra-operative endoscopic image of an anatomical region including an arterial tree and a venous tree; and
an endoscope controller structurally configured to image register the arterial tree within the intra-operative endoscopic image to a pre-operative three-dimensional image of the anatomical region responsive to a generation of the intra-operative endoscopic image of an anatomical region;
wherein the image registration by the endoscope controller includes a venous image matching by the endoscope controller of a graphical representation of each furcation of the venous tree within the intra-operative endoscopic image of the anatomical region to a graphical representation of each furcation of the venous tree within the pre-operative three-dimensional image of the anatomical region;
wherein the image registration by the endoscope controller includes an arterial image matching by the endoscope controller of a graphical representation of each furcation of the arterial tree within the intra-operative endoscopic image of the anatomical region to a graphical representation of each furcation of the arterial tree within the pre-operative three-dimensional image of the anatomical region;
wherein the venous image matching by the endoscope controller includes:
a generation by the endoscope controller of a venous main graph derived from a geometrical representation of the pre-operative three-dimensional image of the anatomical region, the venous main graph including a main set of venous nodes representative of each furcation of the venous tree within the pre-operative three-dimensional image of the anatomical region;
a generation by the endoscope controller of a venous subgraph derived from a geometrical representation of the intra-operative endoscopic image of the anatomical region, the venous subgraph including a subset of the main set of venous nodes and being representative of each furcation of the venous tree within the intra-operative endoscopic image of the anatomical region;
wherein the arterial image matching by the endoscope controller includes:
a generation by the endoscope controller of an arterial main graph derived from a geometrical representation of the pre-operative three-dimensional image of the anatomical region, the arterial main graph including a main set of arterial nodes representative of each furcation of the arterial tree within the pre-operative three-dimensional image of the anatomical region, and
a generation by the endoscope controller of an arterial subgraph derived from a geometrical representation of the intra-operative endoscopic image of the anatomical region, the arterial subgraph including a subset of the main set of arterial nodes and being representative of each furcation of the arterial tree within the intra-operative endoscopic image of the anatomical region;
wherein the endoscope controller is further structurally configured to update the image registration of the intra-operative endoscopic image of the vessel tree to the pre-operative three-dimensional image of the vessel tree responsive to any surgical alteration in a topology of the vessel tree,
wherein the arterial main graph is modified by the endoscope controller to reflect a surgical alteration in the topology of the vessel tree; and
wherein the modifying of the arterial main graph by the endoscope controller includes a connecting by the endoscope controller of an additional node to the main graph, the new node being representative of a surgical creation of an additional furcation of the vessel tree.

4. The image registration system of claim 3, wherein the endoscope controller is further structurally configured to update the image registration of the intra-operative endoscopic image of the vessel tree to the pre-operative three-dimensional image of the vessel tree responsive to any surgical alteration in a topology of the vessel tree.

5. The image registration system of claim 4, wherein the image registration by the endoscope controller further includes a determination by the endoscope controller of a relative positioning of the arterial tree in the pre-operative three-dimensional image of the anatomical region to the venous tree in the pre-operative three-dimensional image of the anatomical region.

6. The image registration system of claim 3, wherein the venous image matching by the endoscope controller includes:
   a generation by the endoscope controller of a venous main graph derived from a geometrical representation of the pre-operative three-dimensional image of the anatomical region, the venous main graph including a main set of venous nodes representative of each furcation of the venous tree within the pre-operative three-dimensional image of the anatomical region, and
   a generation by the endoscope controller of a venous subgraph derived from a geometrical representation of the intra-operative endoscopic image of the anatomical region, the venous subgraph including a subset of the main set of venous nodes and being representative of each furcation of the venous tree within the intra-operative endoscopic image of the anatomical region.

7. The image registration system of claim 3,
   wherein the venous image matching by the endoscope controller further includes a venous node matching by the endoscope controller of the venous subgraph to the venous main graph;
   wherein the arterial image matching by the endoscope controller further includes an arterial node matching by the endoscope controller of the arterial subgraph to the arterial main graph; and
   wherein the image registration further includes a combination of the venous node matching and the arterial node matching.

8. The image registration system of claim 3,
   wherein the image registration by the endoscope controller further includes an integration by the endoscope controller of the venous main graph and the arterial main graph;
   wherein the venous image matching by the endoscope controller further includes a venous node matching by the endoscope controller of the venous subgraph to the integration of the venous main graph and the arterial main graph; and
   wherein the arterial image matching by the endoscope controller further includes an arterial node matching by the endoscope controller of the arterial subgraph to the integration of the venous main graph and the arterial main graph.

9. An image registration system, comprising:
   an endoscope operable for generating an intra-operative endoscopic image of an anatomical region including an arterial tree and a venous tree; and
   an endoscope controller structurally configured to image register the arterial tree within the intra-operative endoscopic image to a pre-operative three-dimensional image of the anatomical region responsive to a generation of the intra-operative endoscopic image of an anatomical region,
   wherein the image registration by the endoscope controller includes a venous image matching by the endoscope controller of a graphical representation of each furcation of the venous tree within the intra-operative endoscopic image of the anatomical region to a graphical representation of each furcation of the venous tree within the pre-operative three-dimensional image of the anatomical region;
   wherein the image registration by the endoscope controller includes an arterial image matching by the endoscope controller of a graphical representation of each furcation of the arterial tree within the intra-operative endoscopic image of the anatomical region to a graphical representation of each furcation of the arterial tree within the pre-operative three-dimensional image of the anatomical region,
   wherein the venous image matching by the endoscope controller includes:
   a generation by the endoscope controller of a venous main graph derived from a geometrical representation of the pre-operative three-dimensional image of the anatomical region, the venous main graph including a main set of venous nodes representative of each furcation of the venous tree within the pre-operative three-dimensional image of the anatomical region, and
   a generation by the endoscope controller of a venous subgraph derived from a geometrical representation of the intra-operative endoscopic image of the anatomical region, the venous subgraph including a subset of the main set of venous nodes and being representative of each furcation of the venous tree within the intra-operative endoscopic image of the anatomical region;
   wherein the arterial image matching by the endoscope controller includes:
   a generation by the endoscope controller of an arterial main graph derived from a geometrical representation of the pre-operative three-dimensional image of the anatomical region, the arterial main graph including a main set of arterial nodes representative of each furcation of the arterial tree within the pre-operative three-dimensional image of the anatomical region, and
   a generation by the endoscope controller of an arterial subgraph derived from a geometrical representation of the intra-operative endoscopic image of the anatomical region, the arterial subgraph including a subset of the main set of arterial nodes and being representative of each furcation of the arterial tree within the intra-operative endoscopic image of the anatomical region;
   wherein the endoscope controller is further structurally configured to update the image registration of the intra-operative endoscopic image of the vessel tree to the pre-operative three-dimensional image of the vessel tree responsive to any surgical alteration in a topology of the vessel tree;
   wherein the arterial main graph is modified by the endoscope controller to reflect a surgical alteration in the topology of the vessel tree; and
   wherein the modifying of the arterial main graph by the endoscope controller includes a disconnecting by the endoscope controller of one of the nodes of the main graph, the disconnected node being representative of a surgical removal of one of the furcations of the vessel tree.

10. An image registration method, comprising:
    generating a pre-operative three-dimensional image of a vessel tree within an anatomical region;
    generating an intra-operative endoscopic image of the vessel tree within the anatomical region; and an endoscope controller image registering the intra-operative endoscopic image of the vessel tree to the pre-operative three-dimensional image of the vessel tree, wherein the image registration by the endoscope controller includes an image matching by the endoscope controller of a graphical representation of each furcation of the vessel tree within the intra-operative endoscopic image of the vessel tree to a graphical representation of each furcation of the vessel tree within the pre-operative three-dimensional image of the vessel tree, the endoscope controller updating the image registration of the intra-operative endoscopic image of the vessel tree to the pre-operative three-dimensional image of the vessel tree responsive to a surgical alteration the vessel tree;

wherein a main graph is modified by the endoscope controller to reflect a change in the topology of the vessel tree;

wherein the modifying of the arterial main graph by the endoscope controller includes (1) a connecting by the endoscope controller of an additional node to the main graph, the new node being representative of a surgical creation of an additional furcation of the vessel tree or (2) a disconnecting by the endoscope controller of one of the nodes of the main graph, the disconnected node being representative of a surgical removal of one of the furcations of the vessel tree.

11. The image registration method of claim 10, further comprising the endoscope controller updating the image registration of the intra-operative endoscopic image of the vessel tree to the pre-operative three-dimensional image of the vessel tree responsive to any surgical variation on the vessel tree.

12. The image registration method of claim 10, wherein the image matching by the endoscope controller includes:

the endoscope controller generating the main graph derived from a geometrical representation of the pre-operative three-dimensional image of the vessel tree, the main graph including a main set of connected nodes representative of each furcation of the vessel tree within the pre-operative three-dimensional image of the vessel tree; and the endoscope controller generating a subgraph derived from a geometrical representation of the intra-operative endoscopic image of the vessel tree, the subgraph including a subset of the main set of connected nodes and being representative of each furcation of the vessel tree within the intra-operative endoscopic image of the vessel tree; and the endoscope controller node matching the subgraph to the main graph.

13. The image registration method of claim 10, wherein the vessel tree is one of an arterial tree and a venous tree.

* * * * *